(12) United States Patent
Simon et al.

(10) Patent No.: US 7,887,259 B2
(45) Date of Patent: Feb. 15, 2011

(54) GEOMORPHOLOGY FOR ENVIRONMENTAL REMEDIATION PROCESSES AND SYSTEMS INCLUDING SEDIMENT SURVEY

(75) Inventors: Philip Simon, Ann Arbor, MI (US); Peter Simon, Ann Arbor, MI (US)

(73) Assignee: Ann Arbor Technical Services, Ann Arbor, MI (US)

( * ) Notice: Subject to any disclaimer, the term of this patent is extended or adjusted under 35 U.S.C. 154(b) by 68 days.

(21) Appl. No.: 11/672,337

(22) Filed: Feb. 7, 2007

(65) Prior Publication Data
US 2007/0286680 A1 Dec. 13, 2007

Related U.S. Application Data

(63) Continuation-in-part of application No. 11/090,538, filed on Mar. 25, 2005, now Pat. No. 7,344,337.

(60) Provisional application No. 60/765,899, filed on Feb. 7, 2006, provisional application No. 60/556,544, filed on Mar. 26, 2004.

(51) Int. Cl.
*B09C 1/00* (2006.01)

(52) U.S. Cl. .................................... 405/128.1

(58) Field of Classification Search ............... 405/128.1
See application file for complete search history.

(56) References Cited

U.S. PATENT DOCUMENTS 7,344,337 B2 * 3/2008 Simon et al. ........... 405/128.15

* cited by examiner

*Primary Examiner*—John Kreck
(74) *Attorney, Agent, or Firm*—Simmons Perrine Moyer Bergman PLC (57) ABSTRACT

The present invention uses one or more sediment survey techniques to map the sediment of a water course in three dimensions. The sediment survey techniques result in sediment definition that may be used to identify zones of sediment (whether areas or volumes) that are likely to contain contaminants. This may be based on the identity of the sediment, the location of the sediment in the water course, the depth of the sediment and/or the thickness of the sediment layer. In one embodiment, the sediment survey techniques, and the resulting sediment definition, may be used in combination with geomorphology techniques to calculate an adjusted contaminant concentration for sediment zones. Based on the adjusted contaminant concentrations for a site, selective sediment removal may be used to achieve the most effective removal of contaminant with the least of sediment removal or sediment testing.

23 Claims, 4 Drawing Sheets

GEOMORPHOLOGY FOR ENVIRONMENTAL REMEDIATION PROCESSES AND SYSTEMS INCLUDING SEDIMENT SURVEY

CLAIM OF PRIORITY

The present application is a continuation in part of U.S. patent application Ser. No. 11/090,538, filed on Mar. 25, 2005 and claims benefit of U.S. patent application Ser. No. 60/765,899, filed on Feb. 7, 2006.

FIELD OF THE INVENTION

The present invention relates generally to the area of remediation of contaminated sediment, and more specifically to processes and systems related to investigation and remediation based on the geomorphology of the site to be remediated.

BACKGROUND OF THE INVENTION

Environmental remediation of water bodies often is an extremely expensive and time consuming process of removing contaminated sediment. Numerous problems exist with traditional techniques. Historically, a dredge or excavation approach has been used to remove all the sediment in a remediation site. Such approaches, while ultimately effective, have two main drawbacks.

First is over-removal of sediment. As well as highly contaminated sediment, relatively uncontaminated sediment will also be removed. Because the dredged or excavated sediment must all be treated as if it were contaminated, the over-removal of sediment leads to increased costs of disposal. Since sediment disposal is one of the major costs of remediation, limiting the amount of sediment removed is desirable.

Second is habitat destruction. The dredge or excavation approach is a rather inexact tool, leading to significant destruction of the physical features and natural habitat in the area that has been remediated. This is particularly true for water courses such as streams, rivers, ponds and lakes. Dredging or excavating may be compared to strip mining where entire areas are scoured bare to capture all the contaminated sediment.

While advances have been made there continues to be a need for techniques that help minimize the amount of sediment removed while being effective to remediate the contamination.

SUMMARY OF THE INVENTION

The present invention uses one or more sediment survey techniques to map the sediment of a water course in three dimensions. The sediment survey techniques result in sediment definition that may be used to identify zones of sediment (whether areas or volumes) that are likely to contain contaminants. This may be based on the identity of the sediment, the location of the sediment in the water course, the depth of the sediment and/or the thickness of the sediment layer. In one embodiment, the sediment survey techniques, and the resulting sediment definition, may be used in combination with geomorphology techniques to calculate an adjusted contaminant concentration for sediment zones. Based on the adjusted contaminant concentrations for a site, selective sediment removal may be used to achieve the most effective removal of contaminant with the least of sediment removal or sediment testing.

DETAILED DESCRIPTION

The present invention comprises methods that help minimize the amount of contaminated sediment that must be removed during remediation of a water course and surrounding area, while also adequately removing the contaminant from the site. Selective removal of sediment reduces the cost of remediation while also minimizing the impact of remediation on the natural environment.

After ongoing contamination has been eliminated, remediation of a water course can begin. Remediation is generally designed to remove contaminant from the water course itself while also ensuring that the water course does not become re-contaminated in the future. To meet these dual goals, the methods of the present invention comprise identifying sediment zones along a water course that are in need of remediation. A sediment zone may be in need of remediation because it contains an unacceptable level of contaminant in the water course (e.g. in-channel, on the banks, on the overbanks, or the like). A sediment zone may also be in need of remediation because it contains contaminant that is likely to be reintroduced into the water course at a future time.

A water course is typically a river, stream, creek, estuary, delta, wetland or the like, whether navigable or not. Water course also includes ponds, lakes, reservoirs, impoundments and the like. Further, water course also includes nearby areas that contact the water, have been covered by water in past or are likely to be covered by water in the future, such as banks, overbanks, flood plains, and the like.

The identification of sediment zones may include determining where sediment is deposited and where sediment is eroded within the water course of interest. Geomorphological principals may be used to identify deposition, erosion and stable zones of the water course. "Applied River Morphology" by Dave Rosgen provides a basic background in geomorphology. This text is incorporated by reference in its entirety. Beyond its ordinary meaning, erosion zone also means an area of the water course that tends to lose material (e.g. sediment) over a given time period, whether that time period is a few hours, a few days, a few weeks, a few months or several years. Beyond its ordinary meaning, deposition zone also means an area of the water course that tends to gain material over a period of time. A stable zone thus is an area that neither loses nor gains material over a given time period. It should be understood that a sediment zone may be an erosion zone during one time period (e.g. during flooding) and a deposition zone during another time period.

In one embodiment, identification of deposition and erosion zones includes comparing images of the water course at differing points in time; preferably several images are compared that have been captured over a number of years (e.g. 5-20 years between the images). More preferably, the images are digital images or digitized images so as to facilitate use with a computer. Aerial images are preferred as giving large scale context to the water course.

Preferably the comparison of aerial photograph allows the determination of how the water course has changed over the period of ongoing contamination. For example, streams and rivers meander over time due to channel bed armoring and lateral movement or due to flooding which creates a preferred flow pattern. Such changes to the water course may be important to identifying deposition, erosion and stable zones of the water course. Sediment that is not now near the flow channel of the course water may have been so at one time, meaning that a former deposition zone may be remote from current deposition zones.

In addition to using images, topographical data (e.g. maps) of the water course and surrounding area are preferably used in identifying the sediment zones. For example, the gradient of the channel may determine whether it is in a deposition zone, an erosion zone or a stable zone. Other data and data collection techniques may also be used to assist in identifying the sediment zones, such as visual inspections of the water course, sediment surveys (as discussed below), identifying the type of sediment in the channel of the water course, and soil profile descriptions. Soil horizon development is similar for geomorphic surfaces that have been subjected to similar parameters such as flooding, scouring, or deposition. Taken to together, the collected information may be mapped to give an output (e.g., a map, graph or chart, or the like) that sets forth the deposition, erosion and stable zones. The output of the identification may be in the form of a tangible media (e.g. paper) or intangible media (e.g. computer readable media) or as information sent to the remediation site (e.g. mapping coordinates to be used by a GPS receiver).

The present invention also comprises using one or more sediment survey techniques to map or image the sediment zones of a site for which remediation is contemplated. Suitable survey techniques include the application of electromagnetic or sonic energy to the sediment of the site. After application of the electromagnetic or sonic energy, the reflected energy is monitored. While any frequency of electromagnetic or sonic energy may be used, some frequencies are more suited to use in sediment survey techniques. For example sonar, radar, lidar, and the like may be used, including their use in such techniques as echo-sounding, sub-bottom profiling sonar, side scan sonar, ground penetrating radar, light detection and ranging, continuous frequency modulating scanning, among other techniques.

Other suitable sediment survey techniques monitor fluctuations in ambient electromagnetic energy over a site in order to derive information about the sediment. For example, monitoring fluctuations in the magnetic field of the site may be used; such monitoring techniques may include the use of magnetometers and/or gradiometers. Of course, monitoring other ambient conditions may also provide useful information such as monitoring radioactivity or monitoring sediment temperature.

The sediment survey techniques discussed herein are preferably useful for surveying sediment zones that are underwater (such as in the thalweg of a water course). However, the survey techniques may also be applied to all sediment zones of a site, whether underwater or not. Surveying of sediment that is under water is particularly desirable because these areas do not lend themselves to visual inspection and otherwise make sediment testing difficult. Furthermore, these techniques can be applied in an efficient manner so that large areas of sediment in a water course may be surveyed in a reasonable amount of time. For example, boat mounted sonar systems are preferably used to survey more than about 0.5 km, more than about 1.0 km, more than about 2.0 km, more than about 5.0 km, more than about 10 km, or more than about 20 km of a water course. Of course, sediment surveys of shorter or longer distances may also be conducted.

Based on the wavelength of the applied energy and the reflection of that energy or based on the fluctuations in ambient energy, information about the identity of the sediment is obtained. For example, silt can be differentiated from pea gravel. Furthermore, the location of the various types of sediment within the water course can be mapped. For example, silt in the main thalweg can be identified and distinguished from pea gravel nearer the bank of the water course. Initially, the sediment survey provides a 2D representation (e.g. a map) of the various sediments on the floor of the water course. This information may be obtained from side scanning sonar mapping of the water course floor, for example.

In addition, the sediment survey can locate the sediment in the third dimensional as well. This identifies the location of the sediment below the surface of the water course and/or below the floor of the water course (e.g. sub-bottom profiling). The advantage of this type of sediment survey is that it also identifies the thickness of sediment layers. With the other information, the volume of sediment of a particular type of sediment may be identified.

Figure 1:
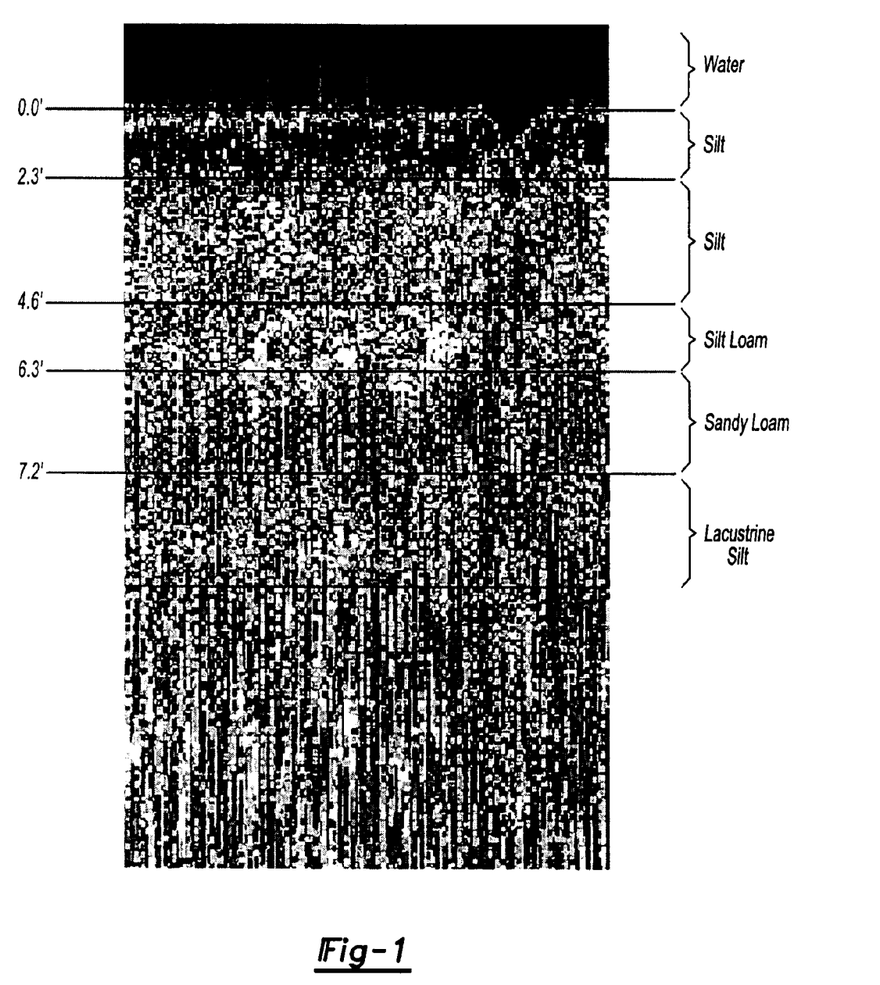
FIGS. 1 and 2 depict the results hydrographic survey of a river bottom with the different t types of sediment being distinguished from one another along with the depth of the sediment.
Figure 2:
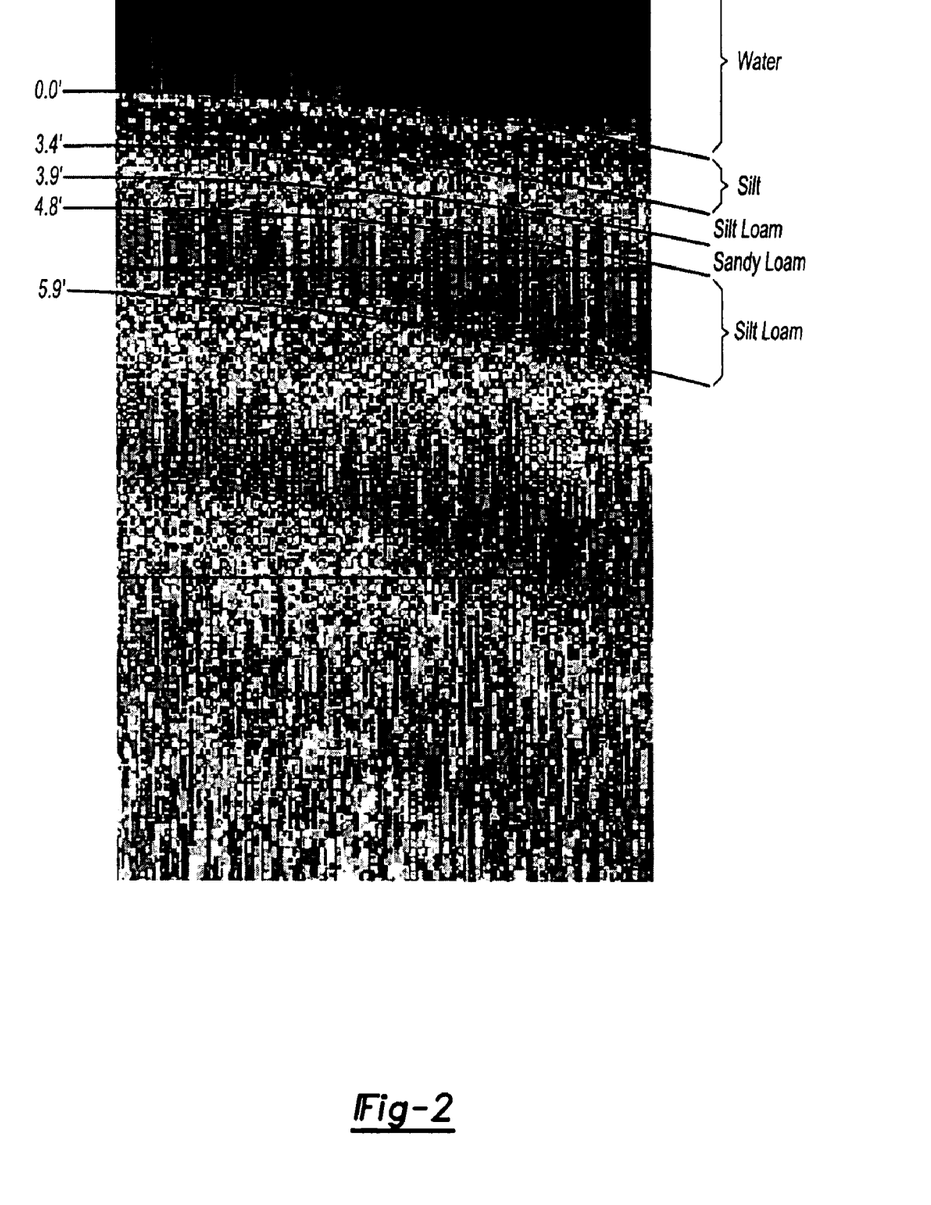
Figure 3:
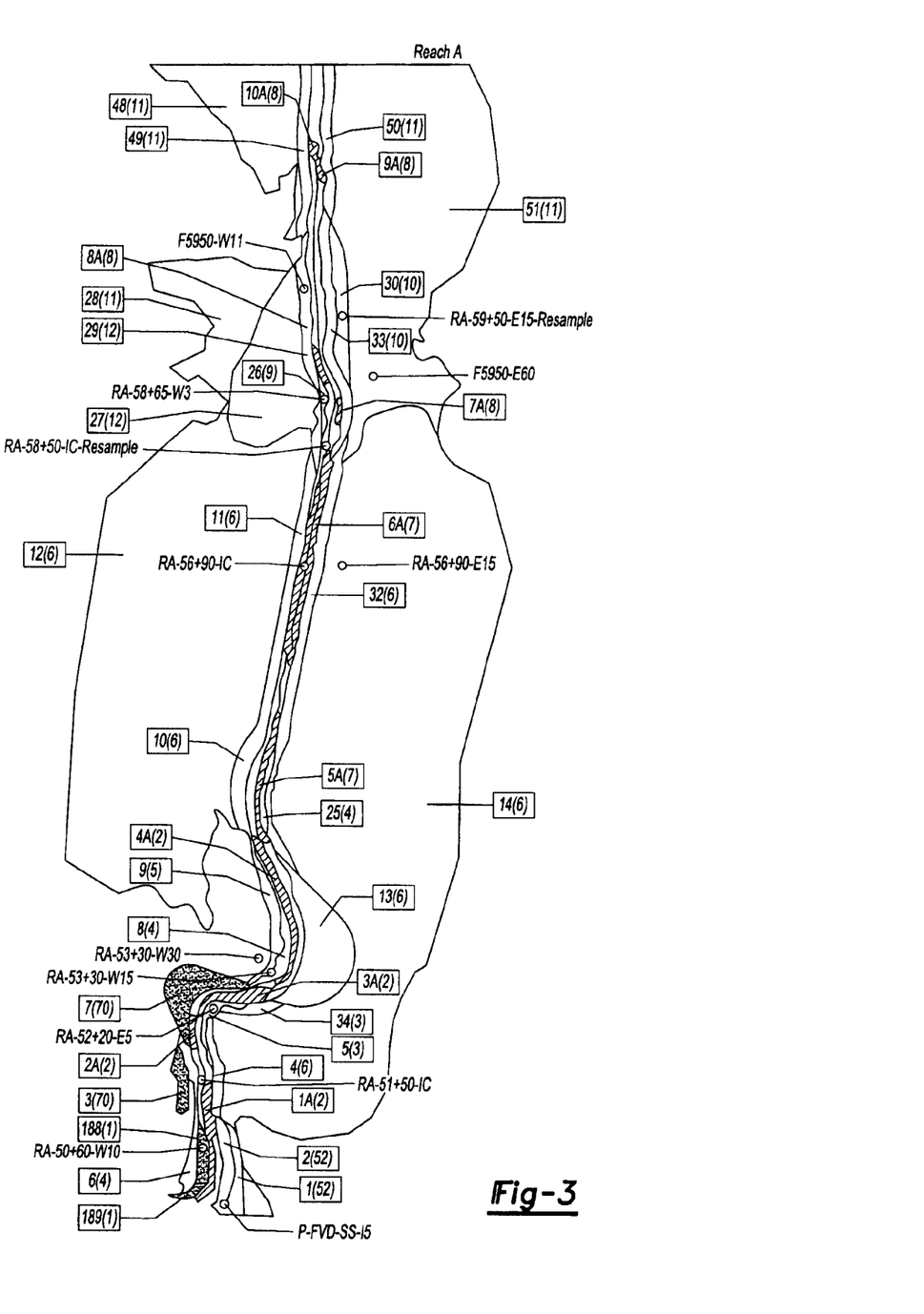
FIG. 3 depicts a remediation site in which adjusted contaminant concentrations have been calculated.
Figure 4:
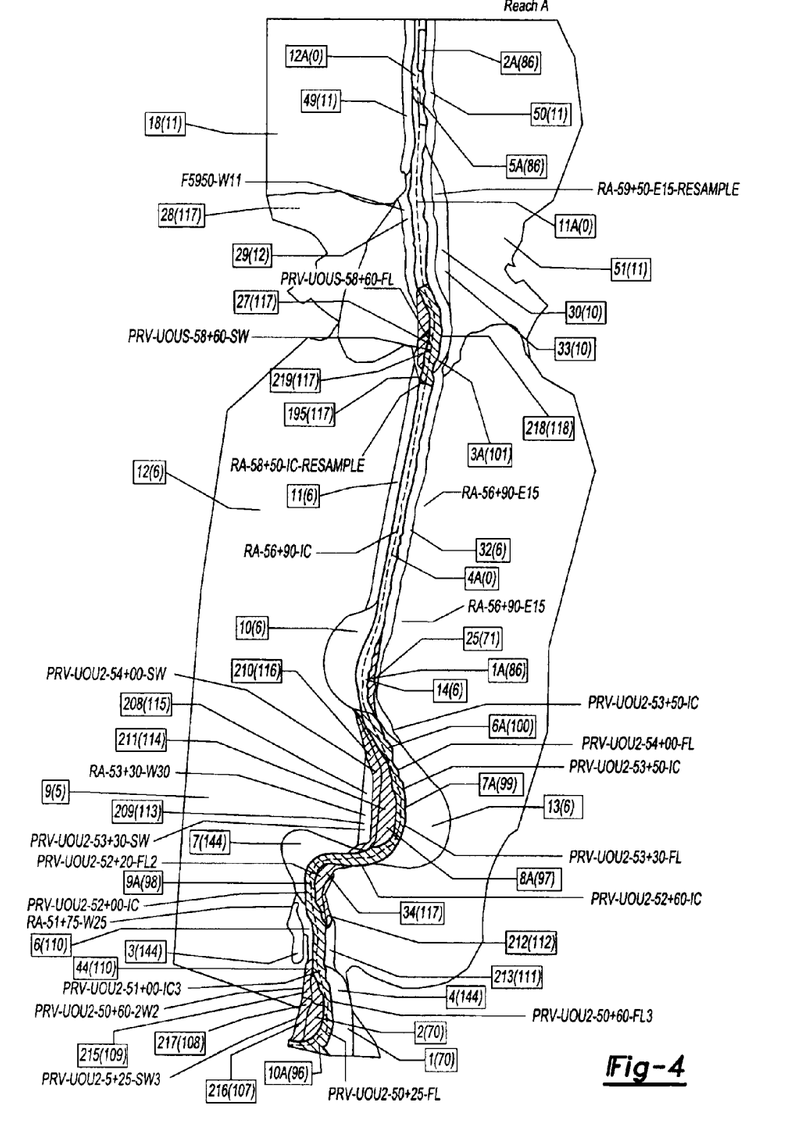
FIG. 4 depicts the remediation site in which post-remediation contaminant concentration have been calculated.

Thus, as depicted in FIGS. 1 and 2, the various sediment layers may be identified as well as the depth and thickness of each layer. As can be seen in FIG. 1, the first layer on the bottom is about 2.3 feet thick and is a silt. The next layer down is also silt of about 2.3 feet thick. Below this is a silt loam of about 1.7 feet thick and a sandy loam of about 0.9 feet thick. The last layer listed is lacustrine loam. The top two layers contain the highest concentrations of contaminant relative the remaining layers; 9.4 and 16 ppm, respectively. Because these layers are exposed to the water or near the water, they are likely to be eroded during times of swift currents and thus to be a source of contaminant that could be reintroduced. Consequently, these layers may be giving a high risk attenuation factor of 1.0. Layer below these two top layers contain relatively minor amounts of contaminants (e.g. <0.01 ppm), and thus do not represent a significant risk of reintroducing contaminants, whether or not they are eroded. For these layers a risk attenuation factor of 0.1 or 0.01 may be applied, depending on whether they are located in an erosion zone, deposition zone or a stable zone. Similarly, FIG. 2 shows a silt layer (about 3.4 feet), followed by a silt loam (about 0.5 feet), a sandy loam (about 0.9 feet) and another silt loam (about 1.1 feet). The top most layer contains a relatively high concentration of contaminant at about 18 ppm and thus is a reintroduction source. Assigning a risk attenuation factor of 1.0 would be appropriate. The second layer has a low concentration of contaminant at 0.25 ppm and thus may be assigned a risk attenuation factor of 0.25, for example. The remaining layers contain relatively low concentration levels of about <0.01 ppm. As above, these layers may be assigned a risk attenuation factor of 0.1 or 0.01 depending on the type of zone the layer is located in.

From the identity of the contaminant and the identity of the sediment, the likelihood that sediment in a particular sediment zone will contain containment can be identified. For example, silt or organic matter is more likely to harbor contaminant than pea gravel. Combining together the information from the sediment survey permits a reduction the number samples that need to be taken, permits adjustments to the adjusted contaminant concentration and/or to the risk attenuation factor, as discussed below. The sediment survey is another technique to reduce the amount of sediment that is removed.

One result of identifying deposition and erosion zones of the water course is the ability to limit the amount of sample testing that needs to be conducted. By understanding where sediment is eroded and deposited, testing may be limited to sediment likely to contain contaminant. Fewer test samples are used due to the understanding of the water course depositional environment. The focus on depositional areas equates to a reduction in the cost of the investigation and the remediation. For example, testing may not be necessary for an erosion zone because any contaminant there will likely have been washed downstream.

Another result of identifying deposition and erosion zones is the ability to identify sediment that may be eroded in the future. Future erosion may lead to reintroduction of the contaminant into the water course.

The identification of sediment zones may include calculating an adjusted concentration of contaminant for each sediment zone. The adjusted concentration of a particular zone incorporates a number of factors including a known or estimated concentration of contaminant (measured in ppm), the area of the zone in square feet, an erosion factor, and a risk attenuation factor.

The concentration of contaminant in a zone may be known by sample testing the sediment of interest. Alternately, the concentration of contaminant in a zone may be estimated. One estimation technique involves the use of a proxy. The known concentration of a contaminant in a proxy zone is assigned to the estimated zone based on similar sediment type, similar relationship to the water course (e.g. in-channel, bank or over bank), similar location with the water course (e.g. proximity to bends and meanders, channel gradient, channel width, etc.). Soft sediment is unconsolidated inorganic/organic material that has settled out of the water course, deposited in the water course, and is easily transportable in the water course under bankfull or flood stage discharge conditions. Non-soft sediment is consolidated inorganic/organic material that is present on the channel bed and is not easily transportable in the water course under bankfull or flood stage discharge conditions. In one preferred embodiment, an estimated concentration of 0.5 ppm may be used for in-channel, non-soft sediments zones, while an estimated concentration of 0.05 ppm may be used for channel bed of bedrock or boulders and cobble. The use of estimated or proxy concentrations is preferred because the technique reduces the amount of sampling that is required.

The erosion factor quantifies the likelihood that sediment will be reintroduced to the water course at some future date. A high erosion factor indicates that the sediment is in the channel of the water course or highly likely to come in contact with water, thus increasing the risk of re-contaminating the water course. On the other hand, a low erosion factor indicates a lower chance that the sediment will be reintroduced into the water in the future.

Assigning the erosion factor takes into account the geomorphology of the water course in question. For water contact areas and areas on the outside of relatively sharp bends, an erosion factor of 1 (high) is used. These areas have the highest erosion factor due to the erosive nature of the thalweg of the water course. The thalweg is the portion of the water course that has the highest velocity and in straight reaches is located in the middle of the water course. In a bend, the thalweg is pushed to the outside of bend, causing the most erosion on the outside of the bend.

For bends that are more gradual, an erosion factor of 0.5 (medium) is used because the full force of the thalweg is not applied against the outside of the bend. An erosion factor of 0.25 (low) is used on banks, the inside of bends and on the overbanks of fairly straight reaches of the water course; some risk of erosion of these areas is present during flood stage. Even though the inside of a bend is usually a deposition zone, it is included here to be conservative. Lastly, areas remote from the water course and areas protected (e.g., boulders, cribbing, revetment, rip-rap, gabions, or the like) in a water course are given an erosion factor of 0.01 (very low). Further reduced erosion factor may also be used for certain bank areas, such as those protected by boulders, cribbing, revetment, rip-rap, gabions, other techniques.

Another factor taken into account in the adjusted concentration is the risk attenuation factor. Remediation activities may skew the tested or estimated concentration of contaminant in a given sediment zone. This is particularly true for sediment zones in the overbank area that are at risk for reintroducing contaminant into the water course after remediation.

Ideally, only clean materials are used to cover contaminated sediment, thus giving a contaminant concentration of zero. However, to be conservative, the risk attenuation factor is applied as follows. If less than two inches of soil cover or rip-rap was used, then a risk attenuation factor of 1 (no attenuation) may be applied; meaning that the soil cover is deemed to provide no attenuation in the risk of re-introduction. If two to six inches of soil cover or rip-rap was used, a risk attenuation factor of 0.5 (low attenuation) may be applied, meaning that the risk of re-introduction has been halved. If more than 6 inches of soil cover or rip-rap was used, a risk attenuation factor of 0.1 (medium attenuation) may be applied. If more than six inches of cover soil or rip-rap is used in combination with a geotextile, than an attenuation factor of 0.01 (high attenuation) may be applied. For example, permanent roads constructed to access the remediation site may utilize clean soil and/or geotextiles and thus attenuate the risk of reintroduction by a significant degree (e.g., 0.01).

An exemplary adjusted concentration for a sediment zone is as follows. A sample taken from a zone in the channel of the water course was tested to have a concentration 1.2 ppm. Because the zone was in the channel an erosion factor of one (high) was applied. Likewise, no cover soil was used in this zone so a risk attenuation factor of one was also applied. In this instance, the adjusted concentration is the same as the starting concentration. In another example, a sample taken from an uncovered zone in the overbank with an initial concentration of 2.6 ppm has an adjusted concentration of 0.026 ppm because the erosion factor is 0.1, while the risk attenuation factor is 0.1.

In one embodiment, sediment surveying techniques are combined with geomorphology to further identify those sediment zones that may be in need of removal. For example, the identity of the sediment is included as a factor in the adjusted contaminant concentration of a sediment zone. Sediments that are likely to contain contaminant are given a relatively high factor or weighting (e.g. 1.0), while sediments that not likely to contain contaminant are given a relatively low factor or weighting (e.g. 0.1 or 0.01).

In addition, the sediment survey may be used to adjust the risk attenuation factor of the adjusted contaminant concentration. For sediment that is likely to contain contaminant (e.g. silt) that is in an erosion zone, a higher risk attenuation factor (e.g. 0.5 or 1.0) may be assigned because the contaminant in this sediment zone is likely to be reintroduced into the water course. On the other hand, a sediment that is likely to contain contaminant, but is under a layer of uncontaminated sediment (e.g. pea gravel) may receive a lower risk attenuation factor (e.g. 0.1 or 0.01) because the risk of reintroduction of this sediment is lower. Likewise, a sediment that is likely to contain contaminant that is in a deposition zone may also receive a lower risk attenuation factor because this sediment is likely to be covered over with subsequent clean sediment and thus the risk of reintroduction will be lower.

One benefit of using sediment surveying techniques is that the volume of the sediment in the sediment zones may be more easily determined. These techniques identify the location of sediment within the vertical sediment layers of the water course. For example, by calculating an adjusted concentration for a volume, the amount of sediment removed may be reduced because sediment layers may be selectively removed, leaving relatively uncontaminated and/or stable sediment while removing the most heavily contaminated sediment or the sediment that is more likely to be disturbed and reintroduce contaminant into the water course.

As can been seen, the adjusted contaminant concentration calculation takes into account the deposition and erosion characteristics of the water course in quantifying the effective amount of contaminant in the sediment. Normalizing and comparing the adjusted concentration to the applicable standard (e.g. site specific requirements, municipal, state or federal laws, regulations, rules or the like) may be used to determine whether a sediment zone needs to be remediated or has been sufficiently remediated.

Identification of sediment zones may also include calculating the area-concentration of each zone from the adjusted concentration and the area, in square feet, of each sediment zone. The area of the sediment zone may be obtained using a Thiessen's polygon approach. The area-concentration quantifies that amount of contaminant at the surface of the sediment zone and gives an overall amount of contaminant in the sediment zone.

The calculation of the area-concentration is summarized in the following formula:

$$C \times EF \times RAF \times A = PA, \text{ where}$$

C=tested or estimated concentration,
EF=erosion factor,
RAF=risk attenuation factor,
A=area of the sediment zone (sq. ft.), and
PA=area-concentration (ppm*sq. ft.).

The area-concentration may be compared with a standard to determine whether a sediment zone needs to be removed or to determine whether the sediment has been sufficiently remediated.

Pre-remediation calculation of the area-concentration of the sediment zones may be used to determine whether it is worthwhile to remove the sediment. Furthermore, post-remediation calculation of the area-concentration may be used to determine whether the remediation was effective.

For example, the area-concentrations of contiguous sediment zones may be collected together to give a surface weighted average concentration (SWAC) for a particular section or reach of the water course. Comparing the pre- and post-remediation SWACs is one method of determining or projecting the effectiveness of a remediation project for that reach.

The SWAC is calculated by dividing the summed area-concentrations for sediment zones in a reach by the summed area of the zones in the reach as represented in the following formula: $\Sigma PA / \Sigma A$.

Some or all of the steps of the methods discussed herein may be carried out or implemented with a computer system. The computer system may include suitable computer executable instructions to carry out any and all the functionality that may be required or desirable to carry out the steps of the disclosed methods or to operate the disclosed systems. The computer system may include computer-executable instructions, computer-readable media, and communication media. Computer-executable instructions (e.g. software and software updates), such as program modules (e.g. routines, programs, objects, components, data structures, and so forth), may be executed by one or more computers or other devices and perform particular tasks or implement particular abstract data types. Computer-executable instructions, such as program modules, may be implemented on, or associated with, various computer-readable media. Communication media typically embody computer-executable instructions, in a modulated data signal such as a carrier wave or other transport mechanism and include any information delivery media. By way of example, and not limitation, communication media include wired media such as a wired network or direct-wired connection, and wireless media such as acoustic, RF infrared, infrared, and the like. Combinations of any of the above should also be included with the scope of computer-readable media.

The present method and systems are suitable for a wide variety of contaminants including polychlorinated bipenyls, pesticides, polynuclear aromatic hydrocarbons, petroleum hydrocarbons, metals, or any other organic, inorganic or organometallic chemical compound which, by one mechanism or another, may become associated with sediments.

For example the contaminant may include one or more compounds from the following classes: acrylamides, acrylic acids and its esters, aldehydes, aliphatic imines, alkanolamines, alkenes, alkylbenzenes, aluminum and its compounds, aminoazobenzenes, azobenzenes, antimony and its compounds, arsenic and its compounds, aryl sulfonic acids and salts, aryl phosphates, azides, inorganic, benzenepolycarboxylates, benzotriazoles, beryllium and its compounds, biphenyl oxides, boron and its compounds, brominated dibenzo-p-dioxins, brominated diphenyl ethers, brominated aromatic compounds, bromobenzenes, bromochloromethanes, cadmium and its compounds, chlorofluorocarbons, chlorofluoroethylenes, chlorinated dibenzofurans, chlorinated paraffins, chlorinated naphthalenes, chlorinated dibenzo-p-dioxins, chlorinated benzenes, chloropentadienes, chlorophenols, chloropropenes, chlorotoluene, chromium and its compounds, cobalt and its compounds, copper and its compounds, creosote, cyclic alkenes, cyclopentadienes, dinitrophenols, dinitrotoluenes, dinitrocresols, epoxides, ethylene oxide, propylene oxide, butylene oxide, ethyl fluorocarbons, fluorides, fluorocarbons, glycols, glycol ethers, glycidyl ethers, haloalcohols, haloethanes, haloethers, halomethanes, halons, haloethylenes, halounsaturated ethanes, hydrochlorofluorocarbons, iron and its compounds, indium and its compounds, inorganic chlorines, inorganic sulfur, ketonic solvents, lead and its compounds, lithium and its compounds, manganese and its compounds, metallocenes, mercaptans, mercaptobenzothiazoles, methacrylic acid and its esters, molybdenum and its compounds, methyl fluorocarbons, methyl ethyl benzene, nickel and its compounds, nitroparaffins, nitroaromatic compounds, nitriles, nicotine and salts, nitrobenzenes, nitroparaffins, nitrophenols, nitrotoluenes, organic acids, organic anhydrides, organic peroxides, organic silicon compounds, organoarsenicals, organoisocyanates, organolead compounds, organomercurials, organophosphate compounds, palladium and its compounds, pesticides, perfluorinated compounds (e.g. perfluorinated carbons), petroleum hydrocarbons, phthalates esters, platinum and its compounds, polychlorinated biphenols, polychlorinated biphenyls, polycyclic organic matter, polyethylene glycolspolynuclear aromatic hydrocarbons, polypropylene glycols, selenium and its compounds, silicones, siloxanes, silver and its compounds, tellurium and its compounds, tetramethylbenzenes, thallium and its compounds, thioureas, titanium and its compounds, trichlorobenzenes, trimethylbenzenes, trinitrophenols, uranium and its compound, xylenols, zinc and its compounds, and combinations thereof.

EXAMPLE

Table 1 shows the pre-remediation data for the overbank areas of the water course illustrated in FIG. 1. Each polygon number is labeled on FIG. 1, as is each sample ID. As can been seen from the table, for each polygon has a contaminant concentration an erosion factor, and a risk attenuation factor. From these, the adjusted contaminant concentration is calculated. With the area of the polygon, the area-concentration for each polygon is calculated. To determine the SWAC, the summed area-concentrations for the polygons is divided by the summed areas of the polygons. For this particular section of the water course, the pre-remediation SWAC is 0.35.

TABLE 1

| Polygon Number (sample #) | Sample ID | Conc. (ppm) | Erosion Factor | Erosion potential | Risk Attenuation Factor | Adjusted Concentration (ppm) | Area (sq. ft.) | PPM × Area (ppm × sq ft) |
|---|---|---|---|---|---|---|---|---|
| 1(52) | P-FVD-SS-I5 | 2.23 | 0.1 | none | 1 | 0.220 | 803.710 | 179.23 |
| 2(52) | P-FVD-SS-I5 | 2.23 | 0.25 | low | 1 | 0.560 | 958.940 | 534.61 |
| 3(70) | I6 | 0.5 | 0.1 | none | 1 | 0.050 | 639.700 | 31.98 |
| 4(6) | RA-56 + 90-E15 | 0.84 | 0.1 | none | 1 | 0.080 | 811.160 | 68.14 |
| 5(3) | RA-52 + 20-E5 | 3.4 | 0.1 | none | 1 | 0.340 | 454.330 | 154.47 |
| 6(4) | RA-53 + 30-W15 | 23 | 0.1 | none | 1 | 2.300 | 1,189.520 | 2,735.90 |
| 7(70) | I6 | 0.5 | 1 | high | 1 | 0.500 | 2,080.630 | 1,040.31 |
| 8(4) | RA-53 + 30-W15 | 23 | 0.25 | low | 1 | 5.750 | 1,020.140 | 5,865.79 |
| 9(5) | RA-53 + 30-W30 | 8.2 | 0.1 | none | 1 | 0.820 | 1,232.590 | 1,010.72 |
| 10(6) | RA-56 + 90-E15 | 0.84 | 0.5 | medium | 1 | 0.420 | 1,620.710 | 680.70 |
| 11(6) | RA-56 + 90-E15 | 0.84 | 0.1 | none | 1 | 0.080 | 2,488.280 | 209.02 |
| 12(6) | RA-56 + 90-E15 | 0.84 | 0.1 | none | 1 | 0.080 | 72,095.220 | 6,056.00 |
| 13(6) | RA-56 + 90-E15 | 0.84 | 1 | high | 1 | 0.840 | 4,997.930 | 4,198.26 |
| 14(6) | RA-56 + 90-E15 | 0.84 | 0.1 | none | 1 | 0.080 | 99,001.050 | 8,316.09 |
| 25(4) | RA-53 + 30-W15 | 23 | 0.25 | low | 1 | 5.750 | 443.700 | 2,551.25 |
| 26(9) | RA-58 + 65-W3 | 46 | 0.1 | none | 1 | 4.600 | 429.050 | 1,973.64 |
| 27(12) | F5950-W11 | 9.1 | 0.1 | none | 1 | 0.910 | 8,950.510 | 8,144.96 |
| 28(11) | F5950-E60 | 2.3 | 0.1 | none | 1 | 0.230 | 8,181.590 | 1,881.77 |
| 29(12) | F5950-W11 | 9.1 | 0.1 | none | 1 | 0.910 | 1,599.910 | 1,455.92 |
| 30(10) | RA-59 + 50-E15-RESAMPLE | 7.1 | 0.1 | none | 1 | 0.710 | 1,685.860 | 1,196.96 |
| 32(6) | RA-56 + 90-E15 | 0.84 | 0.1 | none | 1 | 0.080 | 3,586.620 | 301.28 |
| 33(10) | RA-59 + 50-E15-RESAMPLE | 7.1 | 0.25 | low | 1 | 1.780 | 2,319.050 | 4,116.32 |
| 34(3) | RA-52 + 20-E5 | 3.4 | 0.25 | low | 1 | 0.850 | 464.250 | 394.62 |
| 48(11) | F5950-E60 | 2.3 | 0.1 | none | 1 | 0.230 | 9,156.160 | 2,105.92 |
| 49(11) | F5950-E60 | 2.3 | 0.1 | none | 1 | 0.230 | 1,644.120 | 378.15 |
| 50(11) | F5950-E60 | 2.3 | 0.1 | none | 1 | 0.230 | 1,406.740 | 323.55 |
| 51(11) | F5950-E60 | 2.3 | 0.1 | none | 1 | 0.230 | 39,192.850 | 9,014.36 |
| 188(1) | RA-50 + 60-W10 | 130 | 0.25 | low | 1 | 32.500 | 599.900 | 19,496.78 |
| 189(11) | RA-50 + 60-W10 | 130 | 0.5 | medium | 1 | 65.000 | 166.190 | 10,802.47 |
| | | | | | | Sum | 269,220.410 | 95,219.15 |
| | | | | | | SWAC | 0.35 | |

Table 2 shows post-remediation data for the overbank areas of the water course illustrated in FIG. 2. As in Table 1, each polygon number is labeled on FIG. 2, as is each sample ID.

TABLE 2

| Polygon Number (sample #) | Sample ID | Conc. (ppm) | Erosion Factor | Erosion potential | Risk Attenuation Factor | Adjusted Concentration (ppm) | Area (sq. ft.) | PPM × Area (ppm × sq ft) |
|---|---|---|---|---|---|---|---|---|
| 1(70) | I6 | 0.5 | 0.1 | very low | 1 | 0.050 | 803.710 | 40.19 |
| 2(70) | I6 | 0.5 | 0.25 | low | 1 | 0.125 | 958.940 | 119.87 |
| 3(144) | RA-51 + 75-W25 | 2.1 | 0.1 | very low | 1 | 0.210 | 639.700 | 134.31 |
| 4(144) | RA-51 + 75-W25 | 2.1 | 0.1 | very low | 1 | 0.210 | 491.830 | 103.28 |
| 6(110) | PRV-UOU2-50 + 60-SW2 | 0.03 | 0.1 | very low | 1 | 0.003 | 564.240 | 1.69 |
| 7(144) | RA-51 + 75-W25 | 2.1 | 0.5 | medium | 1 | 1.050 | 2,027.730 | 2,129.12 |
| 9(5) | RA-53 + 30-W30 | 8.2 | 0.1 | very low | 1 | 0.820 | 927.390 | 760.46 |
| 10(6) | RA-56 + 90-E15 | 0.84 | 0.5 | medium | 1 | 0.420 | 3,136.950 | 1,317.52 |
| 11(6) | RA-56 + 90-E15 | 0.84 | 0.1 | very low | 1 | 0.084 | 2,488.280 | 209.02 |
| 12(6) | RA-56 + 90-E15 | 0.84 | 0.1 | very low | 1 | 0.084 | 106,290.320 | 8,928.39 |
| 13(6) | RA-56 + 90-E15 | 0.84 | 0.5 | medium | 1 | 0.420 | 4,997.930 | 2,099.13 |
| 14(6) | RA-56 + 90-E15 | 0.84 | 0.1 | very low | 1 | 0.084 | 98,893.270 | 8,307.03 |
| 25(71) | RA-54 + 90-ES | 5.5 | 0.25 | low | 1 | 1.375 | 443.700 | 610.08 |
| 27(117) | PRV-UOU2-58 + 60-SW | 0.005 | 0.1 | very low | 1 | 0.001 | 8,926.570 | 4.46 |
| 28(117) | PRV-UOU2-58 + 60-SW | 0.005 | 0.1 | very low | 1 | 0.001 | 8,181.590 | 4.09 |
| 29(12) | F5950-W11 | 9.1 | 0.1 | very low | 1 | 0.910 | 1,213.280 | 1,104.08 |
| 30(10) | RA-59 + 50-E15-RESAMPLE | 7.1 | 0.1 | very low | 1 | 0.710 | 1,685.860 | 1,196.96 |
| 32(6) | RA-56 + 90-E15 | 0.84 | 0.1 | very low | 1 | 0.084 | 3,586.620 | 301.28 |
| 33(10) | RA-59 + 50-E15-RESAMPLE | 7.1 | 0.25 | low | 1 | 1.775 | 2,319.050 | 4,116.32 |
| 34(117) | PRV-UOU2-52 + 20-SW2 | 2.9 | 0.25 | low | 1 | 0.725 | 463.940 | 336.36 |
| 48(11) | F5950-E60 | 2.3 | 0.1 | very low | 1 | 0.230 | 26,954.490 | 6,199.53 |
| 49(11) | F5950-E60 | 2.3 | 0.1 | very low | 1 | 0.230 | 1,644.120 | 378.15 |
| 50(11) | F5950-E60 | 2.3 | 0.1 | very low | 1 | 0.230 | 1,406.740 | 323.55 |
| 51(11) | F5950-E60 | 2.3 | 0.1 | very low | 1 | 0.230 | 39,192.860 | 9,014.36 |
| 195(117) | PRV-UOU2-58 + 60-SW | 0.005 | 0.1 | very low | 1 | 0.001 | 113.530 | 0.06 |
| 208(115) | PRV-UOU2-54 + 00-SW | 0.03 | 0.1 | very low | 1 | 0.003 | 648.670 | 1.95 |
| 209(113) | PRV-UOU2-53 + 30-SW | 0.26 | 0.1 | very low | 1 | 0.026 | 479.370 | 12.46 |
| 213(111) | PRV-UOU2-52 + 20-SW2 | 2.9 | 0.1 | very low | 1 | 0.290 | 250.710 | 72.70 |
| 214(110) | PRV-UOU2-50 + 60-SW2 | 0.03 | 0.1 | very low | 1 | 0.003 | 302.500 | 0.91 |
| 217(108) | PRV-UOU2-50 + 25-SW3 | 4.8 | 0.1 | very low | 1 | 0.480 | 481.710 | 231.22 |
| 219(117) | PRV-UOU2-58 + 60-SW | 0.005 | 0.1 | very low | 1 | 0.001 | 354.880 | 0.18 |
| | | | | | | Sum | 320,870.47 | 48,058.73 |
| | | | | | | SWAC | | .015 |

For this particular section of the overbank areas of the water course, the post-remediation SWAC is 0.15, thus indicating an improvement (i.e. reduction) in the amount of contaminant in the section of water course.

It will be further appreciated that functions or structures of a plurality of components or steps may be combined into a single component or step, or the functions or structures of one-step or component may be split among plural steps or components. The present invention contemplates all of these combinations. Unless stated otherwise, dimensions and geometries of the various structures depicted herein are not intended to be restrictive of the invention, and other dimensions or geometries are possible. Plural structural components or steps can be provided by a single integrated structure or step. Alternatively, a single integrated structure or step might be divided into separate plural components or steps. In addition, while a feature of the present invention may have been described in the context of only one of the illustrated embodiments, such feature may be combined with one or more other features of other embodiments, for any given application. It will also be appreciated from the above that the fabrication of the unique structures herein and the operation thereof also constitute methods in accordance with the present invention.

The explanations and illustrations presented herein are intended to acquaint others skilled in the art with the invention, its principles, and its practical application. Those skilled in the art may adapt and apply the invention in its numerous forms, as may be best suited to the requirements of a particular use. Accordingly, the specific embodiments of the present invention as set forth are not intended as being exhaustive or limiting of the invention. The scope of the invention should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes.

What is claimed is:

1. A method for investigating a site for possible selective removal of sediment containing a contaminant, comprising:
   conducting a sediment survey for one or more sediment zones containing sediment in a site containing a water course, wherein conducting the sediment survey comprises 1) applying energy to the one or more sediment zones and monitoring energy reflected by the sediment; 2) monitoring fluctuations in ambient electromagnetic energy of sediment in the one or more sediment zones; 3) monitoring radioactivity of sediment in the one or more sediment zones; 4) monitoring temperature of sediment in the one or more sediment zones; and 5) combinations thereof;
   calculating an adjusted contaminant concentration for each of the one or more sediment zones in the site, by multiplying a known or estimated contaminant concentration by an erosion factor and by a risk attenuation factor; and
   investigating the site for possible selective removal of sediment containing a contaminant based on said conducting step and said calculating step.

2. The method of claim 1 wherein the energy is sonar, radar or lidar.

3. The method of claim 1 wherein the conducting step further comprises identifying the type of sediment, the location of sediment, the volume of sediment and combinations thereof in each of the sediment zones.

4. The method of claim 3 wherein the risk attenuation factor is adjusted based on the type of sediment, the location of sediment, the volume of sediment and combinations thereof.

5. The method of claim 3 further comprising identifying whether the sediment zone is an erosion zone, a deposition zone or a stable zone.

6. The method of claim 1, further comprising determining whether the one or more sediment zone is in need of remediation by comparison of the adjusted contaminant concentration to a standard.

7. The method of claim 6 wherein the standard is a site requirement or a municipal, state or federal law, rule or regulation, and combinations thereof.

8. The method of claim 1 wherein determining the starting concentration comprises estimating the starting concentration or testing the sediment.

9. The method of claim 1 wherein the erosion factor is adjusted based on whether the one or more sediment zones is a deposition zone, an erosion zone or a stable zone.

10. The method of claim 3 wherein identifying sediments zones comprises comparing images of the site that are separated in time, analyzing topographical features of the site, or combinations thereof.

11. The method of claim 10 wherein the identifying step further comprises applying electromagnetic energy to a sediment zone and monitoring energy reflected by the sediment zone.

12. The method of claim 6 further comprising designing a remediation plan based on the determination of which of the one or more sediment zones are in need of remediation.

13. The method of claim 12 further comprising remediating the site in view of the remediation plan.

14. The method of claim 1 wherein the contaminant comprises polychlorinated biphenyls.

15. A method for selective removal of a sediment containing a contaminant, comprising:
   conducting a sediment survey for one or more sediment zones in a site containing a water course;
   assigning a risk attenuation factor, an erosion factor, or both to the one or more sediment zones based on the sediment survey;
   calculating, using a general purpose computer, an adjusted contaminant concentration for each of the one or more sediment zones in the site, by multiplying a known or estimated contaminant concentration by the erosion factor and by the risk attenuation factor; and
   investigating the site for possible selective removal of sediment containing a contaminant based on said conducting step and said calculating step, wherein the investigation step comprises mapping sediments zones in which the adjusted contaminant concentration is above a removal standard.

16. The method of claim 15, further comprising
   designing a remediation plan based on the mapped sediment zones in which the adjusted contaminant concentration is above a removal standard.

17. The method of claim 16 further comprising implementing the designed remediation plan.

18. The method of claim 17 further comprising verifying the implementation of the remediation plan.

19. The method of claim 18 wherein the verifying step comprises postremediation sediment sampling, calculating a post-remediation adjusted contaminant concentration for the one or more sediment zones that have been remediated, a sediment survey or combinations thereof.

20. The method of claim 19 further comprising calculating a surface weighted average concentration for a section of the water course before designing the remediation plan.

21. The method of claim 15 wherein the conducting step comprises applying electromagnetic energy to the sediment zone and monitoring energy reflected by the sediment zone.

22. The method of claim 15 wherein results from the sediment survey comprise, for each sediment zone, one or more of: the type of sediment, the location of sediment, the volume of sediment, whether the sediment zone is an erosion zone, a deposition zone or a stable zone.

23. The method of claim 15 wherein the conducting step comprises using sonar, radar, lidar or combinations thereof.

* * * * *